United States Patent
Kapik et al.

(10) Patent No.: US 9,913,762 B2
(45) Date of Patent: Mar. 13, 2018

(54) SURGICAL TOWELS WITH REDUCED LINT PARTICLE GENERATION

(71) Applicant: Precision Fabrics Group, Inc., Greensboro, NC (US)

(72) Inventors: Rene Kapik, Greensboro, NC (US); Gary Pinkelton, Greensboro, NC (US)

(73) Assignee: Precision Fabrics Group, Inc., Greensboro, NC (US)

( * ) Notice: Subject to any disclaimer, the term of this patent is extended or adjusted under 35 U.S.C. 154(b) by 181 days.

(21) Appl. No.: 14/705,285

(22) Filed: May 6, 2015

(65) Prior Publication Data

US 2015/0335496 A1 Nov. 26, 2015

Related U.S. Application Data

(63) Continuation of application No. 12/478,679, filed on Apr. 23, 2009, now abandoned.

(60) Provisional application No. 61/048,394, filed on Apr. 28, 2008.

(51) Int. Cl.
| | |
|---|---|
| *A61F 13/36* | (2006.01) |
| *D21H 27/00* | (2006.01) |
| *A61F 13/00* | (2006.01) |
| *A61B 90/80* | (2016.01) |
| *A61B 90/70* | (2016.01) |

(52) U.S. Cl.
CPC ........... *A61F 13/36* (2013.01); *D21H 27/007* (2013.01); *A61B 90/70* (2016.02); *A61B 90/80* (2016.02); *A61F 2013/00242* (2013.01); *A61F 2013/00348* (2013.01)

(58) Field of Classification Search
CPC ........... A61F 13/36; A61F 2013/00242; D21H 27/007
See application file for complete search history.

(56) References Cited

U.S. PATENT DOCUMENTS

| | | |
|---|---|---|
| 4,100,324 A | 7/1978 | Anderson et al. |
| 4,425,126 A | 1/1984 | Butterworth et al. |
| 5,308,673 A | 5/1994 | Tochacek et al. |
| 5,571,604 A | 11/1996 | Sprang et al. |
| 2002/0151452 A1 | 10/2002 | Bullock et al. |
| 2004/0175556 A1 | 9/2004 | Clark et al. |
| 2005/0136777 A1 | 6/2005 | Thomaschefsky et al. |
| 2005/0148261 A1 | 7/2005 | Close et al. |
| 2009/0270824 A1 | 10/2009 | Kapik et al. |

FOREIGN PATENT DOCUMENTS

| | | |
|---|---|---|
| EP | 0 373 974 A | 6/1990 |
| FR | 2 467 590 A | 4/1981 |
| GB | 2 221 395 A | 2/1990 |
| WO | WO 00/53835 A1 | 9/2000 |
| WO | WO 00/58539 | 10/2000 |
| WO | WO 02/31260 A2 | 4/2002 |

OTHER PUBLICATIONS

International Search Report and Written Opinion issued by the European Patent Office on Jan. 27, 2010 for the corresponding international application No. PCT/US2009/003893.
International Preliminary Report on Patentability and Written Opinion of the International Searching Authority for International Application No. PCT/US2009/003893; dated Nov. 3, 2011; 10 pages.

*Primary Examiner* — Jeremy R Pierce

(74) *Attorney, Agent, or Firm* — Myers Bigel, P.A.

(57) ABSTRACT

Absorbent surgical towels with reduced lint particle generation are provided. The surgical towels are formed from fibrous substrates containing binder material that limits lint particle generation to 5,000 or less according to INDA standard test 160.1. The binder material can limit lint particle generation to 500 or less.

16 Claims, No Drawings

SURGICAL TOWELS WITH REDUCED LINT PARTICLE GENERATION

RELATED APPLICATIONS

This application is a continuation application of and claims priority to U.S. patent application Ser. No. 12/428,679, filed on Apr. 23, 2009 which claims the benefit of and priority to U.S. Provisional Patent Application No. 61/048,394, filed Apr. 28, 2008, the disclosures of which are incorporated herein by reference in their entirety.

FIELD OF THE INVENTION

The present invention relates generally to towels and, more particularly, to towels used in medical applications.

BACKGROUND

Towels are used widely throughout hospitals and other medical facilities in a variety of ways to assist staff and physicians in absorbing liquids, cleaning surfaces, cushioning, and wiping. These towels are conventionally referred to as "huck" or surgical towels. Conventional surgical towels are woven from cotton spun yarns, and are cut and folded in much the same way as kitchen towels. Although useful for their absorbency, cleaning ability, and soft malleable handle, conventional surgical towels have the tendency to discharge large quantities of cotton particles and fiber during use.

In some cases, the release of particles and lint is not a serious issue. However, when used on or around a surgical wound, the release of particles and lint can cause serious problems including, but not limited to, infection, granuloma, adhesions, thrombosis, embolism, and inflammation. Particles discharged from conventional surgical towels may carry pathogens and may contaminate wounds. When carrying pathogens, the lint particles may be a significant vector of nosocomial infection. Additionally, if particles lodge in a wound they may form adhesions or granulomas that may cause future health problems. In ophthalmic surgical procedures, particles contaminating the wound may cause Diffuse Lamellar Keratitis, which leaves white grainy cells in the eye. Particles also may cause damage if they reside on the surface of an artificial joint implant where they may cause infection and may form scar tissue.

To reduce the potential for contamination, some surgical suites utilize "clean room" technology including the use of lint and particle-free garments, and HEPA filtration. As such, it is counter to good practice to use standard surgical or huck towels in these clean and sterile environments.

Various attempts have been made at producing alternative surgical towels that do not discharge large amounts of lint and particles. See, for example, U.S. Pat. No. 4,275,105 to Boyd; U.S. Pat. No. 5,288,544 to Mallen; U.S. Pat. No. 4,355,066 to Newman; and U.S. Pat. No. 4,075,382 to Chapman. Unfortunately, these alternative designs have failed to produce surgical towels that are absorbent, have good cleaning ability, and have a soft malleable handle, while also solving the problem of lint and particulate contamination.

SUMMARY

In view of the above discussion, improved surgical towels with reduced lint particle generation are provided. In some embodiments, the surgical towels are fibrous substrates finished with a binder material that comprises about 0.5% to about 50% by weight of the fibrous substrate. In some embodiments, the surgical towels are fibrous substrates that include binder fibers that comprise about 0.5% to about 50% by weight of the fibrous substrate. In some embodiments, the surgical towels are fibrous substrates that include binder powder that comprises about 0.5% to about 50% by weight of the fibrous substrate. Surgical towels, according to embodiments of the present invention, can achieve lint particle generation of 5,000 or less according to INDA standard test 160.1. Moreover, in some embodiments, surgical towels can achieve lint particle generation of 2,500 or less, 1,000 or less, and 500 or less.

The surgical towel fibrous substrate, according to embodiments of the present invention, can be a nonwoven fabric, woven fabric, or knitted fabric. Exemplary nonwoven fabrics include, but are not limited to, spunlaced nonwovens, needlepunched nonwovens, carded thermal bonded nonwovens, wet laid nonwovens, spunmelt nonwovens. The fibrous substrate can also be a laminate of at least two separate nonwoven layers that are bonded together (e.g., adhesively bonded, thermally bonded, ultrasonically bonded, joined together via needling, stitching, or spunlacing, etc.). Exemplary fibers forming the fibrous substrate may include, but are not limited to, rayon, lyocell, Tencel, wood pulp, and cotton. In some embodiments, the fibrous substrate includes hydrophobic fibers that have been treated with hydrophilic material. In other embodiments, the fibrous substrate includes absorbent fibers.

In some embodiments, the towel has a weight of less than about 10 ounces per square yard, and an absorbent capacity of greater than about 250%. In some embodiments, the towel has a dry, wet, and solvent crockfastness value of at least a 3 according to AATCC Standard Test Method 8.

In some embodiments, binder material utilizes may include a colorant (e.g., a pigment or dye, etc.). In some embodiments the fibrous substrate may be subjected to one or more of the following operations to increase aesthetics and handle: embossing, creping, mechanically softening, crushing, calendaring, ring rolling, and stretching, etc.

DETAILED DESCRIPTION

The present invention now is described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

According to embodiments of the present invention, improved surgical towels are provided that exhibit significant reductions in linting and particle release and that also provide good absorbency, good cleaning ability, and have a soft malleable handle. Exemplary materials for surgical towels, according to embodiments of the present invention, include nonwoven fabrics and multi-layer laminates of nonwoven fabrics. Suitable nonwoven fabrics may be produced from all of the available nonwoven technologies including, but not limited to, spunlaced, spunbond, needle punched, wet-laid, air laid, thermal bonded, stitchbonded, felted, ultrasonic bonded, resin bonded, and the hybrid mixtures of these processes. Additionally, woven and knitted structures that are treated to create very low linting or particle shedding structures, as described herein, may also be used according to some embodiments of the present invention.

Nonwoven fabrics utilized in surgical towels according to embodiments of the present invention have loft (i.e., some z-direction fiber) and are flexible and strong enough to be used in toweling and absorbing operations. According to some embodiments of the present invention, towel fabric may be produced from 100% of a non-absorbing synthetic fiber such as nylon, polyester, or polypropylene, as long as it is finished or coated with a hydrophilic material that allows the material to adsorb and hold liquids in the interstices of the fabric structure. Suitable hydrophilic materials include hydrophilic binders, surfactants, soil release agents, hydrophilic polymers, solution polymers, exhaustible surfactants, fluorosurfactants, silicone based wetting agents, and the like. In some embodiments, the fabric may contain absorbent fibers, such as rayon, cotton, linen, bamboo, ramie, jute, sisal, wood pulp, wool, silk, or other fiber that can absorb and hold liquid. Absorbency in these materials is inherent in the fiber and does not rinse, or leach from the fabric. The term "absorbent fiber", as used herein, means that liquid is held inside a fiber to some extent and not just held by capillary action in the interstices of the fabric.

Most nonwoven fabric constructions, such as spunlaced, needlepunched, air laid, thermal bond, chemical bond, powder bonded, ultrasonic bonded, felted, stitchbonded, or spunbonded can be used to construct surgical towels according to embodiments of the present invention. However, while many of these nonwoven constructions are acceptable, staple fiber spunlace, thermal bonded, or needlepunched fabrics are preferred.

According to some embodiments of the present invention, the selected towel fabric is treated with a binder material to reduce lint and particle shedding. Binder application is designed to be minimal in keeping with controlling the particle generation and not inhibiting the absorbency of the towel. Solids add-on of from about 0.5% to about 50% is typical (e.g., weight percent add on of binder, solids on solids). As an example, 5% binder means 95% fiber and 5% binder by weight, all solids. The application of the binder can be done with application methods known in the art, such as padding, printing, gravure, flexo, knife coating, foam coating, spraying, slot coating, and the like. Binder application may be done from an aqueous or non-aqueous media. A pigment or dye (collectively referred to as a "colorant") may be added to the binder to allow surgical towels to be produced in various colors (e.g., accepted hospital colors). Alternatively, no dyes or pigments may be added in order to produce a white surgical towel.

According to some embodiments of the present invention, the selected towel fabric may be composed of standard fibers to produce strength, and absorbency, and then bonded using binder fibers or binder powder. A binder fiber is comprised of a polymer that functions like an adhesive binder when incorporated into a web and then thermally activated. Binder fibers are generally formed from polymer that melts at a lower temperature than the main fibers in the web. Binder powder functions in a similar way, but is in particle form. Binder fibers may be all one polymer, or may be coextruded with a polymer that melts higher and maintains the fiber's dimensional stability when the lower melt portion is melted. Core sheath, side by side, "island in sea" and other coextruded shapes may be used. The binder fiber functions by being thermally 'activated' thereby adhesively and mechanically binding the web reducing the particle and fiber shedding.

When used, dyes are selected so as not to crock or bleed from the towel material in normal wet use. A binder used according to embodiments of the present invention may be an emulsion or solution binder, and may be produced from many different polymers including, but not limited to, acrylics, vinyl acetate, vinyl alcohol, ethylene vinyl acetate, urethane, styrene butadiene, alkyds, polyvinyl propylene, maleic anhydride, vinyl chloride, vinylidene chloride, and polyesters.

Applicants have found that soft binders are particularly effective, with decreasing Tg being favored. Glass transition temperature, or Tg, is a measure of stiffness in polymers. Typically binders used in fabric applications range from a low of about −50° C. to about +40° C. All binders can work in this application however, binders below 20° C. are preferred and binders below 0° C., are more preferred. The application of a binder is done to reduce the amount of particle and lint shedding from the fabric and is measured using World Standard Practice 160.1, also known as INDA Standard Test Method 160.1, which is incorporated herein by reference in its entirety.

According to other embodiments of the present invention, a fabric, such as a filament knit or woven fabric, may be constructed in such a way that the INDA 160.1 performance is below 5000 particles, and in such a situation, the fabric would be treated for hydrophilicity, without need for binder.

Surgical towels commonly encountered in the marketplace typically are from about 5-7 ounce/sq. yard in weight. Towels according to embodiments of the present invention are typically lighter in weight but through increased absorbent capacity, can function in an equivalent manner in weight of absorbed material per square area. The weight and structure of surgical towels according to embodiments of the present invention may be achieved by producing a single layer heavy weight nonwoven or by producing a multi layer nonwoven laminate. The laminated towel may be assembled with the aid of an adhesive agent such as an adhesive web, a chemical adhesive, hot melt adhesive, adhesive film or binder fiber. Alternately, the layers may be assembled without adhesive by needling, stitching, thermal bonding, ultrasonic bonding, spunlacing, or by simply serging two layers together at the perimeter. The resulting towel fabric has a weight of from 1.5-10 ounces/sq. yard, and a thickness of from about 0.010" to 0.30".

Comparisons of surgical towels according to some embodiments of the present invention with commercially available surgical towels are illustrated below in Table 1 (comparison with commercially available woven surgical towels) and Table 2 (comparison with commercially available non-woven surgical towels).

TABLE 1

Typical Woven Hospital Towel Data

|  | Diamond Pattern 6001-50000 | Lancelot Pattern 6001-50001 | Woven Cotton A | Woven Cotton B | Woven C | Woven D |
|---|---|---|---|---|---|---|
| Basis Weight | 3.13 | 3.13 | 5.81 | 6.38 | 5.96 | 6.01 |
| Absorbent Rate Sec. | 2.4 | 3.1 | 3.0 | 3.2 | 2 | 6 |
| Absorbent Capacity % | 659.5 | 728.8 | 349.5 | 337.74 | 388.06 | 372.39 |
| (Estimated ounces per sy fabric | 20.6 | 22.8 | 20.3 | 21.5 | 23.13 | 22.38 |
| Linting 0.5 to 10 micron | 413 | 111 | 326,975 | 97,214 | 82,630 | 283,754 |
| Crockfastness-Dry | 4.0 | 4.0 | 4.5 | 4.5 | — | — |
| Crockfastness-Wet | 3.5 | 3.5 | 3.5 | 4.0 | — | — |
| Crockfastness-Solvent | 3.5 | 3.5 | 3.5 | 3.5 | — | — |

TABLE 2

Typical Nonwoven Hospital Towel Data

|  | Diamond Pattern 6001-50000 | Lancelot Pattern 6001-50001 | Nonwoven A | Nonwoven B | Nonwoven C | Nonwoven D |
|---|---|---|---|---|---|---|
| Basis Weight | 3.13 | 3.13 | 3.22 | 2.24 | 2.22 | 3.55 |
| Absorbent Rate Sec. | 2.4 | 3.1 | 2 | 2 | 2 | 1.5 |
| Absorbent Capacity % | 659.5 | 728.8 | 486.72 | 567.22 | 659.77 | 413.39 |
| (Estimated ounces per sy fabric | 20.6 | 22.8 | 15.67 | 12.71 | 14.65 | 14.68 |
| Linting 0.5 to 10 micron | 413 | 111 | 34,397.2 | 5,131 | 10,531.07 | 199,971.2 |
| Crockfastness-Dry | 4.0 | 4.0 | 4.5 | — | — | 5.0 |
| Crockfastness-Wet | 3.5 | 3.5 | 3.5 | — | — | 4.5 |
| Crockfastness-Solvent | 3.5 | 3.5 | 3.5 | — | — | 4.5 |

In the above tables, Crockfastness is measured using AATCC Method 8: "Colorfastness to Crocking; AATCC Crockmeter method; Solvent Crockfastness performed with 70% isopropanol. Absorbancy measured using World Standard Practice 10.1. Particle counts are cumulative average of all particle sizes from 0.5 to 10 micron.

As illustrated above in Tables 1 and 2, the particle discharge of the two surgical towels, according to embodiments of the present invention (i.e., Diamond Pattern 6001-50000 and Lancelot Pattern 6001-50001), is significantly less than any of the conventional surgical towels. Diamond Pattern 6001-50000 and Lancelot Pattern 6001-50001 both exhibit high absorbent capacity and greatly reduced lint particle generation. For example, the absorbent capacity of the Diamond Pattern 6001-50000 is 659.5%, and the absorbent capacity of the Lancelot Pattern 6001-50001 is 728.8%. The lint particle generation (0.5 to 10 micron particles) of the Diamond Pattern 6001-50000 is 413, and the lint particle generation (0.5 to 10 micron particles) of the Lancelot Pattern 6001-50001 is 111.

According to additional embodiments of the present invention, surgical towels may be subjected to various aesthetic treatments including, but not limited to, embossing, creping, mechanically softening, crushing, calendaring, ring rolling, stretching, and the like. These processes are acceptable as long as the low particle generation property is preserved.

The Gelbo-flex linting test measures airborne particles shaken from a fabric per cubic foot of air. The standard protocol for this testing is INDA STM 160.1. Particles are typically measured from 0.5 microns or larger in size. A conventional surgical towel will discharge from about 50,000 to 500,000 particles when shaken according to this test. Surgical towels according to embodiments of the present invention preferably have Gelbo-flex particle counts of less than 5,000, and more preferably less than 2,500, and more preferably less than 1,000, and more preferably less than 500.

TABLE 3

Gelbo Dry Particle Linting vs. Binder Concentration
Fabric Style: 09916, 2.0 osy
Wood Pulp/Polyester

| | Particle Size, microns | | | | | | | |
|---|---|---|---|---|---|---|---|---|
| | 0.5 | 1 | 3 | 6 | 10 | 15 | 20 | 25 |
| Greige Fabric | | | | | | | | |
| Sample #1 | 12,840.0 | 5,970.0 | 550.4 | 50.0 | 14.0 | 9.0 | 7.6 | 5.8 |
| Sample #2 | 52,193.2 | 26,034.0 | 2,333.0 | 194.4 | 49.4 | 28.8 | 21.6 | 17.2 |
| Average | 32,516.6 | 16,002.0 | 1,441.7 | 122.2 | 31.7 | 18.9 | 14.6 | 11.5 |
| 1.0% Binder | | | | | | | | |
| Sample #1 | 4,639.0 | 2,432.2 | 305.0 | 41.2 | 11.0 | 6.8 | 5.0 | 3.8 |
| Sample #2 | 4,997.8 | 3,468.0 | 814.4 | 114.6 | 20.0 | 11.6 | 7.6 | 6.0 |
| Sample #3 | 1,810.4 | 1,328.0 | 362.2 | 52.8 | 11.4 | 5.0 | 3.2 | 2.0 |
| Average | 3,815.7 | 2,409.4 | 493.9 | 69.5 | 14.1 | 7.8 | 5.3 | 3.9 |
| 2.5% Binder | | | | | | | | |
| Sample #1 | 284.2 | 143.0 | 31.8 | 7.2 | 2.0 | 1.4 | 1.4 | 1.0 |
| Sample #2 | 831.0 | 569.0 | 162.6 | 18.4 | 2.2 | 0.6 | 0.4 | 0.4 |
| Sample #3 | 639.4 | 435.2 | 132.2 | 19.2 | 3.6 | 0.8 | 0.6 | 0.6 |
| Average | 584.9 | 382.4 | 108.9 | 14.9 | 2.6 | 0.9 | 0.8 | 0.7 |
| 5.0% Binder | | | | | | | | |
| Sample #1 | 298.0 | 119.6 | 22.6 | 3.4 | 0.8 | 0.4 | 0.2 | 0.2 |
| Sample #2 | 603.6 | 336.0 | 81.6 | 11.6 | 2.4 | 1.6 | 1.4 | 1.2 |
| Sample #3 | 434.4 | 305.6 | 101.4 | 13.4 | 2.2 | 1.0 | 0.6 | 0.6 |
| Average | 445.3 | 253.7 | 68.5 | 9.5 | 1.8 | 1.0 | 0.7 | 0.7 |
| 10.0% Binder | | | | | | | | |
| Sample #1 | 396.2 | 209.4 | 40.8 | 7.4 | 3.2 | 2.6 | 2.0 | 1.6 |
| Sample #2 | 532.0 | 323.0 | 84.6 | 7.0 | 0.6 | 0.2 | 0.2 | 0.2 |
| Sample #3 | 696.8 | 500.2 | 153.4 | 18.6 | 2.6 | 2.0 | 1.4 | 1.0 |
| Average | 541.7 | 344.2 | 92.9 | 11.0 | 2.1 | 1.6 | 1.0 | 0.9 |

Table 3 above illustrates the effectiveness of small amounts of binder to reduce the particle count when producing towel material according to embodiments of the present invention. As illustrated in Table 3, the INDA 160.1 particle counts for greige (unfinished) spunlaced woodpulp/polyester fabric are dramatically reduced with small amounts of binder addition. In addition, the binder concentration decreases the particle counts asymptotically approaching zero. In other words, binder concentration and particle counts are inversely proportional (e.g., as binder concentration increases, particle counts decrease.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A surgical towel comprising an absorbent fibrous substrate having a binder material that limits lint particle generation to 5,000 or less according to INDA standard test 160.1,
   wherein the surgical towel is a nonwoven fabric, and the fibrous substrate comprises one or more nonwoven layers comprising non-absorbing synthetic fibers, a silicone based wetting agent, and the binder material in an amount of about 0.5% to about 10% by weight of the fibrous substrate, and
   wherein the towel has a weight of less than about 10 ounces per square yard and has an absorbent capacity of greater than about 250%.

2. The towel of claim 1, wherein the towel has a thickness of from about 0.010 inch to about 0.30 inch.

3. The towel of claim 1, wherein the binder material is selected from the group consisting of binder fibers and binder powder.

4. The towel of claim 1, wherein the fibrous substrate has a lint particle generation of 2,500 or less according to INDA standard test 160.1.

5. The towel of claim 1, wherein the fibrous substrate has a lint particle generation of 1,000 or less according to INDA standard test 160.1.

6. The towel of claim 1, wherein the fibrous substrate has a lint particle generation of 500 or less according to INDA standard test 160.1.

7. The towel of claim 1, wherein the fibrous substrate comprises a laminate of at least two separate nonwoven layers.

8. The towel of claim 1, wherein the binder material is present in an amount of about 0.5% to about 5% by weight of the fibrous substrate.

9. The towel of claim 1, wherein the towel is bonded by the binder material.

10. The towel of claim 1, wherein the towel is adhesively and mechanically bonded by the binder material.

11. The towel of claim 1, wherein the non-absorbing synthetic fibers are polyester fibers or polypropylene fibers.

12. The towel of claim 1, wherein the fibrous substrate is a laminate of at least two spunlaced woodpulp/polyester layers.

13. The towel of claim 12, wherein the binder material is present in an amount of about 0.5% to about 5% by weight of the fibrous substrate.

14. The towel of claim 12, wherein the towel is bonded by the binder material.

15. The towel of claim 12, wherein the towel is adhesively and mechanically bonded by the binder material.

16. The towel of claim 12, wherein the towel has a weight of less than about 10 ounces per square yard and a thickness from about 0.010 inch to about 0.30 inch.

* * * * *

UNITED STATES PATENT AND TRADEMARK OFFICE
CERTIFICATE OF CORRECTION

PATENT NO. : 9,913,762 B2
APPLICATION NO. : 14/705285
DATED : March 13, 2018
INVENTOR(S) : Kapik et al.

Page 1 of 1

It is certified that error appears in the above-identified patent and that said Letters Patent is hereby corrected as shown below:

On the Title Page

Item (63) Related U.S. Application Data: Please correct "12/478,679" to read -- 12/428,679 --

In the Specification

Column 7, Line 47: Please correct "1.0" to read -- 1.2 --

Signed and Sealed this
Fourteenth Day of August, 2018

Andrei Iancu
*Director of the United States Patent and Trademark Office*